United States Patent [19]

Shishov et al.

[11] Patent Number: 4,583,977

[45] Date of Patent: Apr. 22, 1986

[54] DEVICE FOR LENGTHY FIXATION OF A TUBE INTRODUCED INTO THE PATIENT'S BODY

[75] Inventors: Nikolai M. Shishov; Vladimir E. Zelenetsky; Nadezhda A. Demina; Ivan M. Bondarev; Alexandr N. Cherny; Alisa A. Ertli, all of Moscow; Semen I. Marina, Pushkino; Anatoly G. Avxentiev, Belgorod-Dnestrovsky; Stanislav N. Lepetchenko, Belgorod-Dnestrovsky; Ivan P. Serzhantu, Belgorod-Dnestrovsky, all of U.S.S.R.

[73] Assignee: Vsesojuzny Nauchno-Issledovatelsky Institut Meditsiuskikh Polimerov, Moscow, U.S.S.R.

[21] Appl. No.: 640,822

[22] Filed: Aug. 15, 1984

[51] Int. Cl.[4] ............................................. A61M 5/32
[52] U.S. Cl. ..................................... 604/174; 604/93; 604/175; 128/DIG. 26
[58] Field of Search ........................... 604/174–180, 604/93, 8, 9, 332; 128/154, DIG. 26

[56] References Cited

U.S. PATENT DOCUMENTS

| 2,898,917 | 8/1959 | Wallace | 128/350 |
|---|---|---|---|
| 3,241,554 | 3/1966 | Coanda | 604/178 |
| 3,444,861 | 5/1969 | Schulte | 604/9 |
| 3,575,160 | 4/1971 | Vass | 604/174 |
| 3,577,982 | 5/1971 | La Par | 604/176 |
| 3,782,378 | 1/1974 | Page | 128/DIG. 26 |
| 3,954,105 | 5/1976 | Nordby | 128/154 |
| 4,080,970 | 3/1978 | Miller | 604/174 |
| 4,096,853 | 6/1978 | Weigand | 604/176 |
| 4,250,882 | 2/1981 | Adair | 128/154 |
| 4,393,873 | 7/1983 | Nawash et al. | 604/174 |
| 4,402,681 | 9/1983 | Haas et al. | 604/9 |
| 4,464,178 | 8/1984 | Dalton | 604/174 |
| 4,475,548 | 10/1984 | Muto | 604/167 |
| 4,516,968 | 5/1985 | Marshall et al. | 604/174 |

FOREIGN PATENT DOCUMENTS 2315956 1/1977 France .

Primary Examiner—C. Fred Rosenbaum
Assistant Examiner—Karen L. Kaechele
Attorney, Agent, or Firm—Fleit, Jacobson, Cohn & Price

[57] ABSTRACT

A device for long-term fixation of a tube in the patient's body, including a housing provided with a flexible annular base to secure the tube in the housing, provided with a bushing stationary mounted coaxially with respect to the housing, and ribs connecting the bushing with the flexible annular base and confining a cavity disposed between the base and the patient's body and closed with a cover.

13 Claims, 4 Drawing Figures

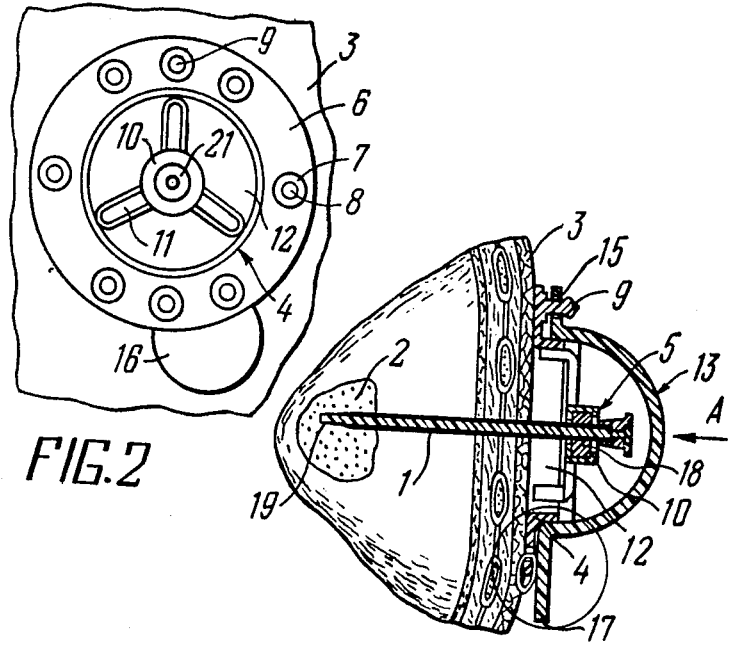
FIG.2
FIG.1
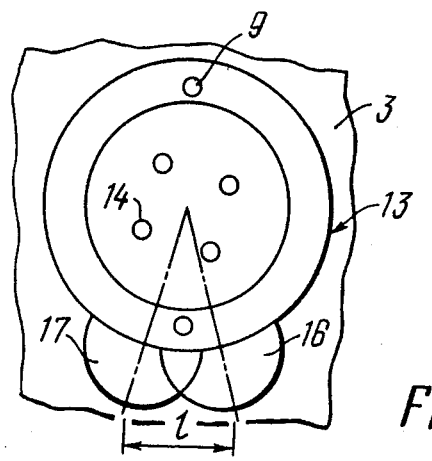
FIG.3
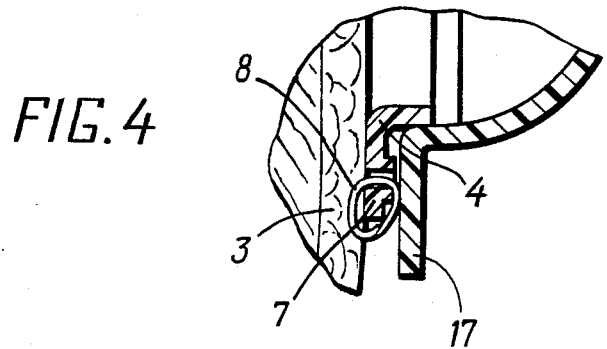
FIG.4

DEVICE FOR LENGTHY FIXATION OF A TUBE INTRODUCED INTO THE PATIENT'S BODY

FIELD OF THE INVENTION

The present invention relates to medical instruments, and more specifically to devices for long-term fixation of a tube introduced into the patient's body.

The present invention can find application in the course of an extended treatment carried out by way of administering medicinal preparations to a patient through a tube introduced into his body for a period of not less than two months. The invention may be successfully used when treating, for instance, cavernous forms of tuberculosis.

BACKGROUND OF THE INVENTION

Known in the art is a device for fixing a tube, such as a drain tube introduced into the patient's body, comprising a housing whose extending portion is made as a cap accomodating a pneumatic annular chamber which contacts and rests upon the patient's body in the intermediate area between the support surface and the tube. The cap and the annular chamber are provided with an opening into which the drain tube is introduced and is clamped therein while some medium, for instance, air under an excessive pressure is filling up the annular chamber. The support portion of the housing is essentially an annular cavity which is depressurized (is under vacuum) to provide for drawing-in of a portion of the skin integument over a circumference. The cap is secured to the patient's body by means of a sticky surface provided on the support portion of the housing, as well as by means of elastic belts (cf. French Patent No. 2,315,956; IPC: A 6I M 3I/00).

However, this device has a number of disadvantages. The support portions of the housing, employed in the device, may cause trauma of the skin integument due to its pressing-in or drawing-in by the support surface, which also results in skin irritation and formation of bedsores particularly during an extended application of the device.

Excretions in the form of sweat drops accumulating on the surface of contact of the support portion of the pneumatic annular chamber made of resin and the patient's body may also cause irritation of the skin integument.

Presence of the pneumatic annular chamber does not allow for a sanitary and hygienic treatment of the skin integument portion at the point of the drain tube introduction without removing the device, which is necessary when the tube is kept in the patient's body for a lengthy time period.

The pneumatic rubber chambers employed in the device complicate the design and the process of manufacture of the product.

Also known in the art is a device for fixing a tube, for example, a drain tube, a catheter, a trocar, etc. in the patient's body, comprising a housing secured to the patient's body and provided with a flexible annular base made as an elastic disk having a central opening.

The housing has an extending portion shaped as a tube which has a branch for inflation. The rubber parts of the housing are interconnected by a permanent joint.

Hermetically mounted inside the tube which is the extending portion of the housing is a resilient bushing the thickness of whose wall is much smaller than that of the wall of the outer tube. The central portion of the bushing is mounted freely, i.e. with some gap in the tube, thereby providing for an annular cavity communicated with the inflating branch. In the course of inflation the central portion of the bushing forms two projections that are disposed opposite each other, clamp and fix the surgical instrument placed into the central opening of the disk. The device is secured to the patient's body with the aid of an adhesive substance (cf. U.S. Pat. No. 2,898,917; NC: 128–350).

The known device has the following disadvantages:

during use of the device there is possible an accidental displacement of the tube while the patient is asleep or as a result of his movement, which may cause pain caused by traumatizing of walls of the cavity by the displaced tube;

strong irritation and damage of the skin integument, which, in its turn, causes strong pain, may take place during an extended contact (for 2–3 months) between the support portion of the housing and the skin integument;

the design of the support portion of the housing does not allow for a sanitary and hygienic treatment of the skin integument at the point of introduction of the tube without removing the device, which is necessary when the tube is kept in the patient's body for a lengthy time period.

Besides, connection of the structure separate parts made of rubber into an integral part is a labour-consuming process.

SUMMARY OF THE INVENTION

It is an object of the present invention to provide a device for long-term fixation of the tube in the patient's body, whose structure would not traumatize walls of the cavity into which the tube is introduced.

Another object of the present invention is to provide conditions for carrying out sanitary and hygienic treatment of the skin integument at the point of introduction of the tube without removing the whole device.

Still another object of the present invention is to provide a device which could be used in out-patients' treatment. Yet another object of the present invention is to provide a device that would not be complicated in manufacture.

These objects are accomplished by that in a device for long-term fixation of a tube introduced into the patient's body, comprising a housing secured to the patient's body and a flexible annular base, and a means for securing the tube in the housing, according to the invention, the means for securing the tube in the housing comprises a bushing stationarily mounted coaxially with the housing, the tube being introduced into the patient's body through the bushing, and ribs connecting the bushing with the flexible annular base and confining a cavity between the flexible annular base and the patient's body for realizing a sanitary and hygienic treatment of the skin integument portion around the tube, the cavity being closed with a cover.

It is expedient to provide the device with a means for removing the cover, made as tabs of which one is disposed on the cover and the other one on the flexible annular base in such a manner that, with the cavity closed with the cover, they displace with respect to each other over a distance providing for a convenient removal of the cover.

It is also expedient to make the cover with a spherical portion having at least one ventilation port made therein.

To secure the whole device to the patient's body, the flexible annular base may have projections with openings made in each of them.

It is expedient to round the free ends of the tabs.

It is also expedient to mount inside the bushing of the means for securing the tube one more bushing made of an elastic material and used for holding the tube introduced into the patient's body.

Use of the device of the present invention makes it possible to eliminate pain during an extended treatment of the patient.

BRIEF DESCRIPTION OF THE DRAWINGS

Other objects and advantages of the present invention will be more readily understood from the following description of its exemplary embodiments and the accompanying drawings, in which:

FIG. I is a sectional view of a device for long-term fixation of a tube introduced into the patient's body, according to the invention;

FIG. 2 shows the same device with the removed cover a view taken along arrow A;

FIG. 3 shows the same device closed with the cover, a view taken along arrow A.

FIG. 4 is an enlarged view of the area circled in FIG. 1.

DETAILED DESCRIPTION OF THE INVENTION

A device for long-term fixation of a tube 1 (FIG. 1) introduced into a cavity 2 of a patient's body 3, comprises a housing 4 secured to the patient's body 3, and a means 5 for securing the tube 1 in the housing 4 (FIGS. 1, 2), with all the parts and units of the device made of a polymeric material.

The housing 4 has a flexible annular base 6 (FIG. 2) provided with projections 7 which are made therein and of which each has an opening 8 for securing the whole device to the patient's body 3 by way, for instance, of placing a silk ligation onto the skin.

The surface of the base 6 is also provided with projections 9 made therein (FIGS. 1, 2).

In accordance with the invention, the means 5 for securing the tube 1 in the housing 4 comprises a bushing 10 (FIG. 1) stationary mounted coaxially with respect to the base 6, and ribs 11 (FIG. 2) which connect the bushing 10 with the base 6 and which mount the bushing 10. Ribs 11 may be of any number, and the invention embodiment under description shows three ribs 11 which are arranged in one and the same plane at an angle of 120° with respect to one another. The ribs 11 are somewhat lifted over the base 6, and, consequently, over the surface of the body 3, thereby simultaneously lifting the bushing 10 too.

The ratio between the height of each rib 11 and its length is selected to be within the range of 1:4-7, which makes the ribs resilient, particularly in the case when they are made of a polymeric material.

The ribs 11 are raised above the base 6 in such a manner that a cavity 12 is formed between the latter and the patient's body 3 around the tube 1. The cavity 12 is closed with a cover 13 (FIGS. 1 and 3) having a spherical portion which is provided with several ventilation ports 14 (FIG. 3) made therein. The cover 13 has an end face having openings 15 made therein, the number of the openings 15 corresponding to the number of the projections 9 (FIGS. 1, 2), and the latter entering the openings 15 when the cavity 12 is closed with the cover 13 in the manner shown in FIG. 1.

The device is also provided with a means for removing the cover 13, which is made as tabs 16 and 17 (FIGS. 2, 3). The tab 16 is disposed on the flexible base 6, and the tab 17 is disposed on the cover 13, whereby, with the cavity 12 closed with the cover 13, the tabs 16 and 17 will necessarily be displaced with respect to each other in such a manner that there will be some distance "1" between their axes, said distance making it possible for the servicing personnel, by having conveniently gripped the tab 17 disposed on the cover 13 and by holding the other tab 16 (by pressing it against the patient's body), to remove the cover 13 without damaging the fixation of the introduced tube or causing unpleasant feelings on the part of the patient. To decrease traumatizing, the free ends of the tabs 16 and 17 are made rounded.

Mounted inside the bushing 10 (FIGS. 1, 2) is another bushing 18 which is made of an elastic material and holds the tube 1 after it has been introduced into the cavity 2 of the patient's body 3, the tube 1 being rigidly secured in the bushing 18.

In order to place and fix the tube 1 in the patient's body 3, it is necessary to perform the following:

The bushing 18 and the tissue of the patient's body are punched at a required spot with a stiletto (not shown in the drawing) having the tube 1 tightly adhering thereto. The device is moved along the tube 1 until the base 6 contacts the skin of the patient; whereupon the base 6 is secured to the patient's body by way, for example, of placing through the openings 8 in the projections 7 a silk ligation onto the skin. With the base 6 secured, the stiletto is removed and the tube 1 remains in the body 3 of the patient.

To prevent the tube 1 from accidental displacement when the patient is asleep or during his movement, the cover 13 is positioned on the base 6 in such a manner that the projections 9 of the base 6 are closely aligned with the respective openings 15 in the cover 13. Thereby, the cavity 12 confined by the patient's body 3 portion and the base around the tube 1 will be closed. However, owing to the ventilation ports 14 the cavity 12 is communicated with atmosphere, which makes it possible to eliminate almost comletely any maceration of the skin integument on this portion of the body.

Elimination of possible displacements of the tube is achieved due to the resilience of the ribs 11 and the resilience of the device as a whole, as it is made of polymeric materials.

To eliminate the possiblity of appearance of pneumothorax and to determine the position of the tube 1, the latter has a mandrin 19 (FIG. 1) made of a roentgen-contrast material, introduced therein.

To remove the cover 13, it is sufficient to press the tab 16 against the body 3 and pull the tab 17 which is either secured to or made integral with the cover 13, whereupon the projections 9 will leave one after the other the openings 15, and the cover 13 will be removed to make an access to the tube 1. During all this the patient feels no pain, and it is possible to treat easily and quickly the portion of the skin integument around the tube 1.

Thus, the device under description makes it possible to eliminate the possibility of accidental displacements of the tube introduced into the patient's body for a lengthy time period, thereby doing away with pain caused by traumatizing walls of the cavity by the displaced tube.

The device provides for a convenient access to the tube, prevents maceration of the skin integument around the tube and allows for a sanitary and hygienic treatment of the wound formed during an extended stay of the tube in the cavity.

The device is simple to manufacture, for example, by the method of injection moulding.

What is claimed is:

1. A device for long-term fixation of a tube introduced into a patient's body, said device comprising:
   a housing secured to the patient's body;
   a flexible annular base of said housing;
   securing means for securing said tube in said housing, said securing means including
      a first bushing mounted stationary and coaxially with said housing and through which said tube is introduced into the patient's body;
      at least two identical ribs, each rib connecting said bushing with said flexible annular base and each rib made so that in combination they define a cavity between the patient's body and said flexible annular base;
      said cavity intended for sanitary and hygienic treatment of a skin integument portion formed around said tube introduced into the patient's body; and
   a cover closing said cavity and connected with said flexible annular base.

2. A device as claimed in claim 1, further comprising removal means for removing said cover, said removal means including a first tab and a second tab; said first tab being radially located on said cover; said second tab being radially located on said flexible annular base so that when said cover is fixed on said flexible annular base, said second tab is located, in relation to said first tab, offset at a distance sufficient for convenient removal of said cover by the lifting of said first tab while said second tab is held stationary.

3. A device as claimed in claim 1, wherein said flexible annular base is provided with at least two projections and a respective number of openings, each opening being defined by a respective projection and said openings being used for long-term securing of the device to the patient's body by stitching said flexible annular base to said body with stitching material applied to the patient's skin through said openings.

4. A device as claimed in claim 2, wherein said cover includes a spherical portion and at least one ventilation port made in said spherical portion.

5. A device as claimed in claim 2, wherein said first and second tabs have their free ends rounded.

6. A device for long-term fixation of a tube introduced into a patient's body, said device comprising:
   a housing secured to the patient's body;
   a flexible annular base of said housing;
   securing means for securing said tube in said housing, said securing means including
      a first bushing mounted stationarily and coaxially with said housing and through which said tube passes when said tube is introduced into the patient's body;
      at least two identical ribs, each rib connecting said bushing with said flexible annular base, said rib, being made so that in combination they form a cavity between the patient's body and said flexible annular base, said cavity being intended for sanitary treatment of the area of the patient's skin integument around said tube introduced into the patient's body;
      a second bushing made of resilient material and placed within said first bushing, said second bushing holding said tube after it is inserted into the patient's body; and
   a cover closing said cavity and connecting with said flexible annular base.

7. A device as claimed in claim 6, further comprising removal means for removing said cover, said removal means including a first tab and a second tab; said first tab being radially located on said cover; said second tab being radially located on said flexible annular base so that when said cover is fixed on said flexible annular base, said second tab is located, in relation to said first tab, offset at a distance sufficient for convenient removal of said cover by the lifting of said first tab while said second tab is held stationary.

8. A device as claimed in claim 6, wherein said flexible annular base is provided with at least two projections and a respective number of openings, each opening being defined by a respective projection and said openings being used for long-term securing of the device to the patient's body by stitching said flexible annular base to said body with stitching material applied to the patient's skin through said openings.

9. A device as claimed in claim 7, wherein said cover includes a spherical portion and at least one ventilation port made in said spherical portion.

10. A device as claimed in claim 7, wherein said first and second tabs have their free ends rounded.

11. A device for long-term fixation of a tube introduced into a patient's body, said device comprising:
    a housing secured to the patient's body;
    a flexible annular base of said housing;
    securing means for securing said tube in said housing, said securing means including
       a first bushing mounted stationarily and coaxially with said housing and through which said tube passes when said tube is introduced into the patient's body;
       at least two identical ribs, each rib connecting said bushing with said flexible annular base, each said rib being made so that in combination they form a cavity between the patient's body and said flexible annular base, said cavity being intended for sanitary treatment of the area of the patient's skin integument around said tube introduced into the patient's body;
       a second bushing made of resilient material and placed within said first bushing, said second bushing holding said tube after it is inserted into the patient's body;
    a cover closing said cavity and connected with said flexible annular base;
    removal means for removing said cover having the form of a first tab and a second tab, said first tab being radially located on said cover, said second tab being radially located on said flexible annular base in such a manner that, with said cover being fixed on said flexible annular base, said second tab is offset with relation to said first tab by a distance that provides for convenient removal of said cover by the lifting of said first tab while said second tab is held stationary; and said flexible annular base provided with at least two projections and a respective number of openings, each opening being formed in a respective projection, and said openings being used for securing the device by application of stitching material to the patient's skin through said openings.

12. A device as claimed in claim 11, wherein said cover includes a spherical portion and at least one ventilation port made in said spherical portion.

13. A device as claimed in claim 11, wherein said first and second tabs have their free ends rounded.

* * * * *